United States Patent
Stanley et al.

(10) Patent No.: US 9,422,209 B2
(45) Date of Patent: Aug. 23, 2016

(54) PROPYLENE VIA METATHESIS WITH LOW OR NO ETHYLENE

(71) Applicant: Lummus Technology Inc., Bloomfield, NJ (US)

(72) Inventors: Stephen J. Stanley, Matawan, NJ (US); Robert J. Gartside, Summit, NJ (US); Thulusidas Chellppannair, East Brunswick, NJ (US)

(73) Assignee: Lummus Technology Inc., Bloomfield, NJ (US)

( * ) Notice: Subject to any disclaimer, the term of this patent is extended or adjusted under 35 U.S.C. 154(b) by 300 days.

(21) Appl. No.: 14/024,986

(22) Filed: Sep. 12, 2013

(65) Prior Publication Data

US 2014/0081061 A1    Mar. 20, 2014

Related U.S. Application Data

(60) Provisional application No. 61/701,144, filed on Sep. 14, 2012.

(51) Int. Cl.
*C07C 6/04* (2006.01)
*C07C 5/25* (2006.01)

(52) U.S. Cl.
CPC ............... *C07C 6/04* (2013.01); *C07C 5/2512* (2013.01); *C07C 2521/10* (2013.01); *C07C 2523/02* (2013.01); *C07C 2523/24* (2013.01); *C07C 2523/32* (2013.01)

(58) Field of Classification Search
CPC ............. C07C 6/00; C07C 6/02; C07C 6/04
USPC .............. 585/647, 643, 644, 646, 314
See application file for complete search history.

(56) References Cited

U.S. PATENT DOCUMENTS 2,657,245 A * 10/1953 Davidson .................. C07C 2/20
585/510

4,410,753 A    10/1983 Reid et al.
(Continued)

FOREIGN PATENT DOCUMENTS

EP        1854776 A1     11/2007
JP    2005519131 A      6/2005
(Continued)

OTHER PUBLICATIONS

International Search Report and Written Opinioin issued Dec. 24, 2013 in corresponding International Application No. PCT/US2013/059260 (10 pages).
(Continued)

*Primary Examiner* — In Suk Bullock
*Assistant Examiner* — Sharon Pregler
(74) *Attorney, Agent, or Firm* — Osha Liang LLP (57) ABSTRACT

A process for producing propylene is disclosed, including: fractionating a mixed C4 hydrocarbon stream to recover a first fraction comprising isobutene and a second fraction comprising 2-butene; contacting the first fraction with a first metathesis catalyst in a first metathesis reaction zone; recovering an effluent from the first metathesis reaction zone comprising at least one of ethylene, propylene, unreacted isobutene, C5 olefins, and C6 olefins; contacting the second fraction and the ethylene in the effluent with a second metathesis catalyst in a second metathesis reaction zone; recovering an effluent from the second reaction zone comprising at least one of unreacted ethylene, propylene, unreacted 2-butene, fractionating the effluent from the first metathesis reaction zone and the effluent from the second metathesis reaction zone to recover an ethylene fraction, a propylene fraction, one or more C4 fractions, and a fraction comprising at least one of C5 and C6 olefins.

12 Claims, 7 Drawing Sheets

(56) References Cited

U.S. PATENT DOCUMENTS

| | | |
|---|---|---|
| 5,087,780 A | 2/1992 | Arganbright |
| 5,321,193 A | 6/1994 | Lin et al. |
| 5,321,194 A | 6/1994 | Apelian et al. |
| 5,382,743 A | 1/1995 | Beech, Jr. et al. |
| 5,898,091 A | 4/1999 | Chodorge et al. |
| 6,075,173 A | 6/2000 | Chodorge et al. |
| 6,130,181 A | 10/2000 | Schwab et al. |
| 6,136,289 A | 10/2000 | Szabo et al. |
| 6,271,430 B2 | 8/2001 | Schwab et al. |
| 6,358,482 B1* | 3/2002 | Chodorge ............ C07C 5/2556 585/643 |
| 6,580,009 B2 | 6/2003 | Schwab et al. |
| 6,583,329 B1* | 6/2003 | Podrebarac ............ C07C 6/04 585/643 |
| 6,683,019 B2 | 1/2004 | Gartside et al. |
| 6,727,396 B2 | 4/2004 | Gartside |
| 6,777,582 B2 | 8/2004 | Gartside et al. |
| 7,214,841 B2 | 5/2007 | Gartside et al. |
| 7,223,895 B2 | 5/2007 | Sumner |
| 2003/0009072 A1* | 1/2003 | Gartside ............... C07C 5/2512 585/670 |
| 2010/0041930 A1* | 2/2010 | Gartside ................ C07C 4/06 585/314 |

FOREIGN PATENT DOCUMENTS

| | | |
|---|---|---|
| JP | 2007531696 A | 11/2007 |
| JP | 2008519033 A | 6/2008 |
| JP | 2012500304 A | 1/2012 |
| JP | 2012502057 A | 1/2012 |
| JP | 2012520348 A | 9/2012 |
| WO | 02100535 A1 | 12/2002 |
| WO | 03/076371 A1 | 9/2003 |
| WO | 2010028267 A2 | 3/2010 |

OTHER PUBLICATIONS

Extended European Search Report issued Mar. 16, 2016 in corresponding European application No. 13837451.7 (4 pages).

Office Action issued in Japanese Application No. 2015-532022; Dated Jun. 7, 2016 (8 pages).

* cited by examiner

PROPYLENE VIA METATHESIS WITH LOW OR NO ETHYLENE

CROSS-REFERENCE TO RELATED APPLICATIONS

This application, pursuant to 35 U.S.C. §119(e), claims priority to U.S. Provisional Application Ser. No. 61/701,144, filed Sep. 14, 2012, which is incorporated by reference in its entirety.

FIELD OF THE DISCLOSURE

Embodiments disclosed herein relate generally to the production of propylene via metathesis using low or no fresh ethylene.

BACKGROUND

In typical olefin plants, such as illustrated in U.S. Pat. No. 7,223,895, there is a front-end demethanizer for the removal of methane and hydrogen followed by a deethanizer for the removal of ethane, ethylene and $C_2$ acetylene. The bottoms from this deethanizer tower consist of a mixture of compounds ranging in carbon number from $C_3$ to $C_6$. This mixture may be separated into different carbon numbers, typically by fractionation.

The $C_3$ cut, primarily propylene, is removed as product and is ultimately used for the production of polypropylene or for chemical synthesis such as propylene oxide, cumene, or acrylonitrile. The methyl acetylene and propadiene (MAPD) impurities must be removed either by fractionation or hydrogenation. Hydrogenation is preferred since some of these highly unsaturated $C_3$ compounds end up as propylene thereby increasing the yield.

The $C_4$ cut, consisting of $C_4$ acetylenes, butadiene, iso- and normal butenes, and iso- and normal butane can be processed in many ways. A typical steam cracker $C_4$ cut contains the following components in weight %:

TABLE 1

Typical $C_4$ cut components and weight percentages.

| | |
|---|---|
| $C_4$ Acetylenes | Trace |
| Butadiene | 33% |
| 1-butene | 15% |
| 2-butene | 9% |
| Isobutylene | 30% |
| Iso- and Normal Butanes | 13% |

The components in a refinery or FCC based $C_4$ cut are similar, with the exception that the percentage of paraffins are considerably greater.

Typically, the butadiene and $C_4$ acetylenes are removed first. This can be accomplished by either hydrogenation or extraction. The product from butadiene and $C_4$ acetylene removal is designated Raffinate I. If extraction is employed, the remaining 1-butene and 2-butene remain essentially in the same ratio as that of the initial feedstock. If hydrogenation is employed, the initial product from butadiene hydrogenation is 1-butene. Subsequently, hydroisomerization occurs within the same reaction system changing the 1-butene to 2-butene. The extent of this reaction depends upon catalyst and reaction conditions within the hydrogenation system. However, it is common practice to limit the extent of hydroisomerization in order to avoid "over hydrogenation" and the production of butanes from butenes. This would represent a loss of butene feedstock for downstream operations. The butenes remaining in the mixture consist of normal olefins (1-butene, 2-butene) and iso-olefins (isobutylene). The balance of the mixture consists of both iso- and normal-butanes from the original feed plus what was produced in the hydrogenation steps and any small quantity of unconverted or unrecovered butadiene.

A Raffinate I stream can be further processed in many ways. A Raffinate II stream is by definition a stream following isobutylene removal. Isobutylene can be removed in a number of ways. It can be removed via fractionation. In fractionation isobutane will be removed along with the isobutylene. In addition, some fraction of the 1-butene will be lost as well. The resultant Raffinate II will contain primarily normal olefins and paraffins and minimal isoolefins and isoparaffins. Isobutylene can also be removed via reaction. Reactions include: reaction with methanol to form MTBE, reaction with water to form tertiary butyl alcohol, or reaction with itself to form a $C_8$ gasoline component. In all reaction cases, the paraffins are not removed, and thus the mixture will contain both normal and isoparaffins. The paraffin content and composition of the Raffinate II impacts downstream processing options.

The butenes have many uses. One such use is for the production of propylene via metathesis. Another is for the production of ethylene and hexene via metathesis. Conventional metathesis involves the reaction of normal butenes (both 1-butene and 2-butene) with ethylene (principally the reaction of 2-butene with ethylene to form propylene). These reactions occur in the presence of a group VIA or VIIA metal oxide catalyst, either supported or unsupported. The paraffin components of the reaction feed are essentially inert and do not react, and are typically removed from the process via a purge stream in the separation system that follows the metathesis reactor. Typical catalysts for metathesis are tungsten oxide supported on silica or rhenium oxide supported on alumina. Examples of catalysts suitable for the metathesis of olefins are described in U.S. Pat. No. 6,683,019, for example. Isobutylene (isobutene) may be removed from the feedstock prior to the metathesis reaction step. The reaction of isobutylene with ethylene is non-productive and reaction with itself and/or other $C_4$'s is limited in the presence of excess ethylene. Non-productive reactions essentially occupy catalyst sites but produce no product. If allowed to remain in the feed to the metathesis unit, the concentration of this non-reactive species would build up creating capacity limitations. The reaction of 1-butene with ethylene is also non-productive. However, it is common to employ a double bond isomerization catalyst within the metathesis reactor to shift 1-butene to 2-butene and allow for continued reaction. Typical double bond isomerization catalysts include basic metal oxides (Group IIA), either supported or unsupported. Magnesium oxide and calcium oxide are examples of such double bond isomerization catalysts that may be physically admixed with the metathesis catalyst. No equivalent co-catalyst exists for the skeletal isomerization of isobutylene to normal butene. In the case of a conventional metathesis system employing both a metathesis catalyst and a co-mixed double bond isomerization catalyst, the butadiene must be removed to a level of less than 500 ppm to avoid rapid fouling of the double bond isomerization catalyst. The metathesis catalyst itself can tolerate butadiene levels up to 10,000 ppm.

In some cases, an isobutylene removal step is employed prior to metathesis. Options include reacting it with methanol to produce methyl tertiary butyl ether (MTBE) or separating the isobutylene from the butenes by fractionation.

U.S. Pat. No. 6,358,482 discloses the removal of isobutylene from the $C_4$ mixture prior to metathesis. This scheme is further reflected in U.S. Pat. Nos. 6,075,173 and 5,898,091. U.S. Pat. No. 6,580,009 discloses a process for the production of propylene and hexene from a limited ethylene fraction. For molar ratios of ethylene to butenes (expressed as n-butenes) from 0.05 to 0.60, the inventors utilize a Raffinate II stream as the $C_4$ feedstock.

The typical metathesis process takes the Raffinate I feedstock and removes the majority of the isobutylene via fractionation, as described above to form a Raffinate II. In this step, the isobutene is removed as well plus some quantities of normal butenes, dependent upon the fractionation conditions. The Raffinate II is then admixed with ethylene, passed through guard beds to remove poisons, vaporized and preheated and fed to the metathesis reactors. The operating conditions are typically 300° C. and 20 to 30 bar pressure. The reactor effluent following heat recovery is then separated in a fractionation system. First the ethylene is recovered overhead in a first tower and recycled to the reactor system. The tower bottoms are then sent to a second tower where the propylene is recovered overhead. A side draw is taken containing the majority of the unconverted $C_4$ components and recycled to the reactor. The tower bottoms containing the $C_5$ and heavier products plus $C_4$ olefins and paraffins are sent to purge. The purge rate is typically fixed to contain sufficient $C_4$ paraffins to avoid their buildup in the reactor recycle stream. In some cases, a third tower is employed on the tower bottoms stream to separate the $C_4$ components overhead and the $C_5$ and heavier components as a bottoms stream.

U.S. Pat. No. 6,271,430 discloses a two-step process for the production of propylene. The first step consists of reacting 1-butene and 2-butene in a raffinate II stream in an auto-metathesis reaction to form propylene and 2-pentene. The products are then separated in the second step. The third step reacts specifically the 2-pentene with ethylene to form propylene and 1-butene. This process utilizes the isobutylene free raffinate II stream. The pentenes recycled and reacted with ethylene are normal pentenes (2-pentene).

Isobutylene removal from the $C_4$ stream can also be accomplished by employing a combined catalytic distillation hydroisomerization deisobutyleneizer system to both remove the isobutylene and recover n-butenes at high efficiency by isomerizing the 1-butene to 2-butene with known isomerization catalysts and thus increasing the volatility difference. This technology combines conventional fractionation for isobutylene removal with hydroisomerization within a catalytic distillation tower. In U.S. Pat. No. 5,087,780 to Arganbright, 2-butene is hydroisomerized to 1-butene as the fractionation occurs. This allows greater than equilibrium amounts of 1-butene to be formed as the mixture is separated. Similarly, 1-butene can be hydroisomerized to 2-butene in a catalytic distillation tower. In separating a $C_4$ stream containing isobutylene, 1-butene, and 2-butene (plus paraffins), it is difficult to separate isobutylene from 1-butene since their boiling points are very close. By employing simultaneous hydroisomerization of the 1-butene to 2-butene with fractionation of isobutylene, isobutylene can be separated from the normal butenes at high efficiency.

The metathesis reaction described above is equimolar, i.e., one mole of ethylene reacts with 1 mole of 2-butene to produce 2 moles of propylene. However, commercially, in many cases, the quantity of ethylene available is limited with respect to the quantity of butenes available. In addition, the ethylene is an expensive feedstock and it is desired to limit the quantities of ethylene used. As the ratio of ethylene to butenes is decreased, there is a greater tendency for the butenes to react with themselves which reduces the overall selectivity to propylene.

The metathesis catalysts and the double bond isomerization catalysts are quite sensitive to poisons. Poisons include water, $CO_2$, oxygenates (such as MTBE), sulfur compounds, nitrogen compounds, and heavy metals. It is common practice to employ guard beds upstream of the metathesis reaction system to insure the removal of these poisons. It does not matter if these guard beds are directly before the metathesis reaction system or further upstream as long as the poisons are removed and no new poisons are subsequently introduced.

Metathesis reactions are very sensitive to the location of the olefin double bond and the stereo-structure of the individual molecules. During the reaction, the double bond on each pair of olefins adsorb on the surface and exchange double bond positions with the carbon groups on either sides of the double bonds. Metathesis reactions can be classified as productive, half productive or non-productive. As described above, non-productive reactions result in essentially no reaction taking place. When the double bonds shift with metathesis reaction, the new molecules are the same as the originally adsorbed molecules thus no productive reaction occurs. This is typical for reactions between symmetric olefins or reactions between ethylene and alpha olefins. If fully productive reactions occur, new products are generated no matter which orientation the molecules occupy the sites. The reaction between ethylene and 2-butene to form two propylene molecules is a fully productive reaction. Half productive reactions are sterically inhibited. If the pair of olefins adsorb in one orientation (typically the cis position with respect to the attached R groups), when the double bonds shift, new products are formed. Alternately if they adsorb in a different steric configuration (the trans position), when the bonds shift, the identical olefins are formed and thus no new products are formed. The various metathesis reactions proceed at different rates (a fully productive reaction is usually faster than a half productive reaction). Table 2 summarizes the reactions between ethylene and various butenes and the reactions between the butenes themselves.

The reactions listed in Table 2 represent the base reaction with ethylene (reaction 1, 4 and 5) as well as the reactions between the various $C_4$ olefins. It is especially important to make a distinction between the selectivity to propylene from total $C_4$ olefins (including isobutylene) and the selectivity to propylene from the normal $C_4$ olefins involved in the reaction. The reaction of isobutylene with 2-butene (reaction 6) produces propylene and a branched $C_5$ molecule. For this reaction, propylene is produced at 50 molar % selectivity from total $C_4$'s (similar to reaction 2) but at a 100 molar % selectivity from the normal $C_4$ (2-butene). For the purposes of definitions, conventional metathesis is defined as the reaction of the $C_4$ olefin stream with ethylene. However, the $C_4$ stream can also react in the absence of ethylene as a feedstock. This reaction is called auto or self metathesis. In this case, reactions 2, 3, 6, and 7 are the only possible reactions and will occur at rates dependent upon the feedstock composition.

TABLE 2

| No. | Reaction | Type | Rate | Molar % Selectivity ($C_3H_6$ from total $C_4$s) | Molar % Selectivity ($C_3H_6$ from n-$C_4$s) |
|---|---|---|---|---|---|
| 1 | 2-butene + ethylene → 2 propylene (Conventional Metathesis) | Fully Productive | Fast | 100 | 100 |
| 2 | 1-butene + 2-butene → Propylene + 2-pentene | Fully Productive | Fast | 50 | 50 |
| 3 | 1-butene + 1-butene → Ethylene + 3-hexene | Half Productive | Slow | 0 | 0 |
| 4 | Isobutylene + Ethylene → No reaction | Non-productive | No Reaction | — | — |
| 5 | 1-butene + ethylene → No reaction | Non-productive | No Reaction | — | — |
| 6 | Isobutylene + 2-butene → Propylene + 2-methyl 2-butene | Fully Productive | Fast | 50 | 100 |
| 7 | Isobutylene + 1-butene → ethylene + 2-methyl 2 pentene | Half productive | Slow | 0 | 0 |

In conventional metathesis, the focus is to maximize reaction 1 to produce propylene. This will maximize the selectivity to propylene. As such, excess ethylene is used to reduce the extent of the reactions of butenes with themselves (reactions 2, 3, 6, and 7). The theoretical ratio is 1/1 molar or 0.5 weight ratio of ethylene to n-butenes but it is common in conventional metathesis to employ significantly greater ratios, typically, 1.3 or larger molar ratio to minimize reactions 2, 3, 6 and 7. Under conditions of excess ethylene, and due to the fact that both isobutylene and 1-butene do not react with ethylene (see reactions 4 and 5), two process sequences are employed. First, the isobutylene is removed prior to metathesis. If isobutylene is not removed, it will build up as the n-butenes are recycled to achieve high yield. Second, 1-butene is isomerized to 2-butene by including a double bond isomerization catalyst such as magnesium oxide admixed with the metathesis catalyst. Note that this catalyst will not cause skeletal isomerization (isobutylene to normal butylenes) but only shift the double bond from the 1 position to the 2 position for the normal butenes. Thus by operating with excess ethylene, eliminating isobutylene from the metathesis feed prior to reaction, and employing a double bond isomerization catalyst, reaction 1 is maximized. Note, however, that by removing the isobutylene, potential production of propylene or other products is lost.

When there is limited or no fresh ethylene (or excess butylenes for the ethylene available), there are currently two options available for propylene production. In these cases, the first option will first remove the isobutylene and then process the normal butenes with whatever ethylene is available. The entire n-butenes-only mixture is subjected to metathesis with the available ethylene. Ultimately, if there is no fresh ethylene available, the $C_4$'s react with themselves (auto metathesis). Under low ethylene conditions, reactions 2, 3, 6 and 7 will occur, all leading to a lower propylene selectivity (50% or lower versus 100% for reaction 1). The lower selectivity results in lower propylene production. Note that reactions 6 and 7 will be minimized as a result of the removal of isobutylene (to low levels but not necessarily zero). Alternatively, the molar flows of ethylene and butenes can be matched by limiting the flow of butenes to produce conditions where there is a high selectivity of the normal butenes to propylene via reaction 1. By limiting the flow of n-butenes to match ethylene, the production of propylene is limited by the reduced butenes flow.

Pentenes and some hexenes are formed to some extent in the conventional metathesis case with low ethylene via reactions 2 and 3. The volume of these components will depend upon the ethylene/n-butenes ratio with a lower ratio producing more $C_5$ and $C_6$ components. In the conventional prior art case where isobutylene is removed before any metathesis, these $C_5$ and $C_6$ olefins are normal olefins since no skeletal isomerization occurs. It is possible to recycle these olefins back to the metathesis step where, for example, the reaction with ethylene and 2-pentene will occur yielding propylene and 1-butene. The 1-butene is recovered and recycled. Note however, with limited ethylene, reaction 1 can occur only to the limit of the ethylene availability. Ultimately these non-selective byproducts, pentenes and hexenes, must be purged from the system.

U.S. Pat. No. 6,777,582 discloses a process for the auto-metathesis of olefins to produce propylene and hexene. Therein, auto-metathesis of a mixed normal butenes feed in the presence of a metathesis catalyst operates without any ethylene in the feed mix to the metathesis reactor. Some fraction of the 2-butene feed may be isomerized to 1-butene and the 1-butene formed plus the 1-butene in the feed react rapidly with the 2-butene to form propylene and 2-pentene. The feed to the reactor also includes the recycle of the 2-pentene formed in the reactor with unreacted butenes to simultaneously form additional propylene and hexene. The 3-hexene formed in the reaction may be isomerized to 1-hexene.

In U.S. Pat. No. 6,727,396, ethylene and hexene-1 are produced from butene-1 by metathesis of butene-1 and isomerization of the hexene-3 produced therein to hexene-1. The initial starting material is a mixed butene stream wherein butene-1 is isomerized to butene-2 with isobutylene being separated therefrom, followed by isomerization of butene-2 to butene-1, with the butene-1 being the feed to the metathesis.

In U.S. Pat. No. 7,214,841, the $C_4$ cut from a hydrocarbon cracking process is first subjected to auto-metathesis prior to any isobutylene removal and without any ethylene addition, favoring the reactions which produce propylene and pentenes. The ethylene and propylene produced are then removed leaving a stream of the $C_4$s and heavier components. The $C_5$ and heavier components are then removed leaving a mixture of 1-butene, 2-butene, isobutylene, and iso- and normal butanes. The isobutylene is next removed preferably by a catalytic distillation hydroisomerization deisobutyleneizer. The isobutylene-free $C_4$ stream is then mixed with the product ethylene removed from the autometathesis product together with any fresh external ethylene needed and subjected to conventional metathesis producing additional propylene.

Processes to produce propylene using low or no ethylene are of interest due to the limited commercial availability of ethylene, especially with respect to the quantity of butenes commercially available. Also, ethylene is an expensive feedstock and limiting the quantities of ethylene used may result in significant cost savings. However, as the ratio of ethylene to butenes is decreased, there is a greater tendency for the butenes to react with themselves, which reduces the overall selectivity to propylene.

SUMMARY OF THE DISCLOSURE

Embodiments disclosed herein relate to the production of propylene when processing a $C_4$ cut from a hydrocarbon cracking process when the supply of ethylene is limited. The $C_4$ cut has typically had butadiene removed to a level where the inlet concentration is less than 10,000 ppm (a Raffinate I stream).

In one aspect, embodiments disclosed herein relate to a process for producing propylene, including: fractionating a mixed C4 hydrocarbon stream to recover a first fraction comprising isobutene and a second fraction comprising 2-butene; contacting at least a portion of the first fraction with a first metathesis catalyst in a first metathesis reaction zone; recovering an effluent from the first metathesis reaction zone comprising at least one of ethylene, propylene, unreacted isobutene, C5 olefins, and C6 olefins; contacting at least a portion of the second fraction and at least a portion of the ethylene in the effluent with a second metathesis catalyst in a second metathesis reaction zone; recovering an effluent from the second reaction zone comprising at least one of unreacted ethylene, propylene, unreacted 2-butene, fractionating the effluent from the first metathesis reaction zone and the effluent from the second metathesis reaction zone to recover an ethylene fraction, a propylene fraction, one or more C4 fractions, and a fraction comprising at least one of C5 and C6 olefins.

In another aspect, embodiments disclosed herein relate to a process for producing propylene, including: fractionating a mixed C4 hydrocarbon stream to recover a first fraction comprising isobutene and 1-butene and a second fraction comprising 2-butene; contacting at least a portion of the first fraction with a first metathesis catalyst in a first metathesis reaction zone; recovering an effluent from the first metathesis reaction zone comprising at least one of ethylene, propylene, unreacted isobutene, unreacted 1-butene, C5 olefins, and C6 olefins; fractionating the effluent from the first metathesis reaction zone to recover a fraction comprising ethylene and propylene, a fraction comprising any unreacted isobutene and any unreacted 1-butene, and a fraction comprising any C5 and C6 olefins; contacting at least a portion of the second fraction and ethylene with a second metathesis catalyst in a second metathesis reaction zone; recovering an effluent from the second reaction zone comprising at least one of unreacted ethylene, propylene, and unreacted 2-butene, fractionating the effluent from the second metathesis reaction zone and the fraction comprising ethylene and propylene to recover an ethylene fraction, a propylene fraction, a C4 fraction, and a fraction comprising at least one of C5 and C6 olefins; feeding at least a portion of the ethylene fraction to the second metathesis reaction zone as the ethylene; feeding at least a portion of the C4 fraction to the second metathesis reaction zone; and feeding at least a portion of the fraction comprising any unreacted isobutene and any unreacted 1-butene to the first metathesis reaction zone.

In another aspect, embodiments disclosed herein relate to a process for producing propylene, including: feeding a mixed C4 hydrocarbon stream comprising 1-butene, 2-butene, and isobutene to a catalytic distillation reactor system; concurrently in the catalytic distillation reactor system: isomerizing at least a portion of the 2-butene to form 1-butene; fractionating the mixed C4 hydrocarbon stream to recover a first fraction comprising isobutene and 1-butene and a second fraction comprising 2-butene; and contacting at least a portion of the first fraction with a first metathesis catalyst in a first metathesis reaction zone; recovering an effluent from the first metathesis reaction zone comprising at least one of ethylene, propylene, unreacted isobutene, C5 olefins, and C6 olefins; contacting at least a portion of the second fraction and at least a portion of the ethylene in the effluent with a second metathesis catalyst in a second metathesis reaction zone; recovering an effluent from the second reaction zone comprising at least one of unreacted ethylene, propylene, unreacted 2-butene, fractionating the effluent from the first metathesis reaction zone and the effluent from the second metathesis reaction zone to recover an ethylene fraction, a propylene fraction, one or more C4 fractions, and a fraction comprising at least one of C5 and C6 olefins.

Other aspects and advantages will be apparent from the following description and the appended claims.

DETAILED DESCRIPTION

Embodiments disclosed herein relate generally to the production of propylene via metathesis of $C_4$ olefins using low or no fresh ethylene. Under those cases where the molar ratio of ethylene to the $C_4$ stream is zero or less than 0.5 weight ratio or 1.0 molar ratio, the $C_4$ stream is processed more efficiently and the total propylene made from a steam cracker or fluid catalytic cracker $C_4$ stream that contains isobutylene and isobutane can be increased according to embodiments disclosed herein by first fractionating the $C_4$ feed to produce an isobutylene fraction and a 2-butene fraction, employing an autometathesis step to react the isobutylene to form ethylene (e.g., reaction 5). The ethylene produced may then be used in a second conventional metathesis reaction system to react the ethylene with the 2-butene stream. Depending upon the relative concentration of the $C_4$ olefins and paraffins (n-butane, isobutane), various separation schemes may be used to fractionate the respective metathesis products to result in the ethylene fraction, a product propylene fraction, one or more C4 recycle fractions, and one or more C5 and/or C6 product fractions.

Processes according to embodiments disclosed herein advantageously produce ethylene from isobutylene according to the following reaction (Reaction 8):

Isobutylene+Isobutylene→Ethylene+2,3-dimethyl-2-butene (8).

In addition to Reaction 8, other embodiments disclosed herein may produce ethylene via Reaction 2 (1-butene+isobutylene→ethylene+2-methyl-2-pentene). The performance of the automethathesis may vary depending upon the relative compositions of isobutylene, 1-butene, and 2-butene in the $C_4$ stream.

In other embodiments, the ratio of isobutylene, 1-butene, or 2-butene in the $C_4$ stream may be adjusted using skeletal isomerization (1-butene↔isobutylene) or positional isomerization (1-butene↔2-butene) where the type of isomerization or preferred product may depend on the particular $C_4$ stream used. The isomerization or skeletal isomerization may be performed using a fixed bed or catalytic distillation reactor system. In other embodiments, the concentration (ratio) of isobutylene may be adjusted using an isobutylene stream as may be readily available in some hydrocarbon processing plants.

In some embodiments, the hydrocarbon feed to processes disclosed herein may be supplied as a mixed $C_4$ stream. The mixed $C_4$ feed to processes disclosed herein may include $C_3$ to $C_{6+}$ hydrocarbons, including $C_4$, $C_4$ to $C_5$, and $C_4$ to $C_6$ cracker effluents, such as from a steam cracker or a fluid catalytic cracking (FCC) unit. Other refinery hydrocarbon streams containing a mixture of $C_4$ olefins may also be used. When $C_3$, $C_5$ and/or $C_6$ components are present in the feed, the stream may be pre-fractionated to result in a primary $C_4$ cut, a $C_4$ to $C_5$ cut, or a $C_4$ to $C_6$ cut.

$C_4$ components contained in the feed stream may include n-butane, isobutane, isobutene, 1-butene, 2-butene, and butadiene. In some embodiments, the mixed $C_4$ feed is pretreated to provide a 1-butene feed for the metathesis reaction. For example, when butadiene is present in the $C_4$ feed, the butadiene may be removed via hydrogenation or extraction. In other embodiments, the mixed butenes feed following or in conjunction with butadiene hydrogenation may be subjected to hydroisomerization conditions to convert 1-butene to 2-butene, with isobutylene being separated from a 2-butene stream by fractionation. The 2-butene stream may then be isomerized back to 1-butene in a subsequent step for use as feed to the metathesis portion of the processes disclosed herein.

Figure 1:
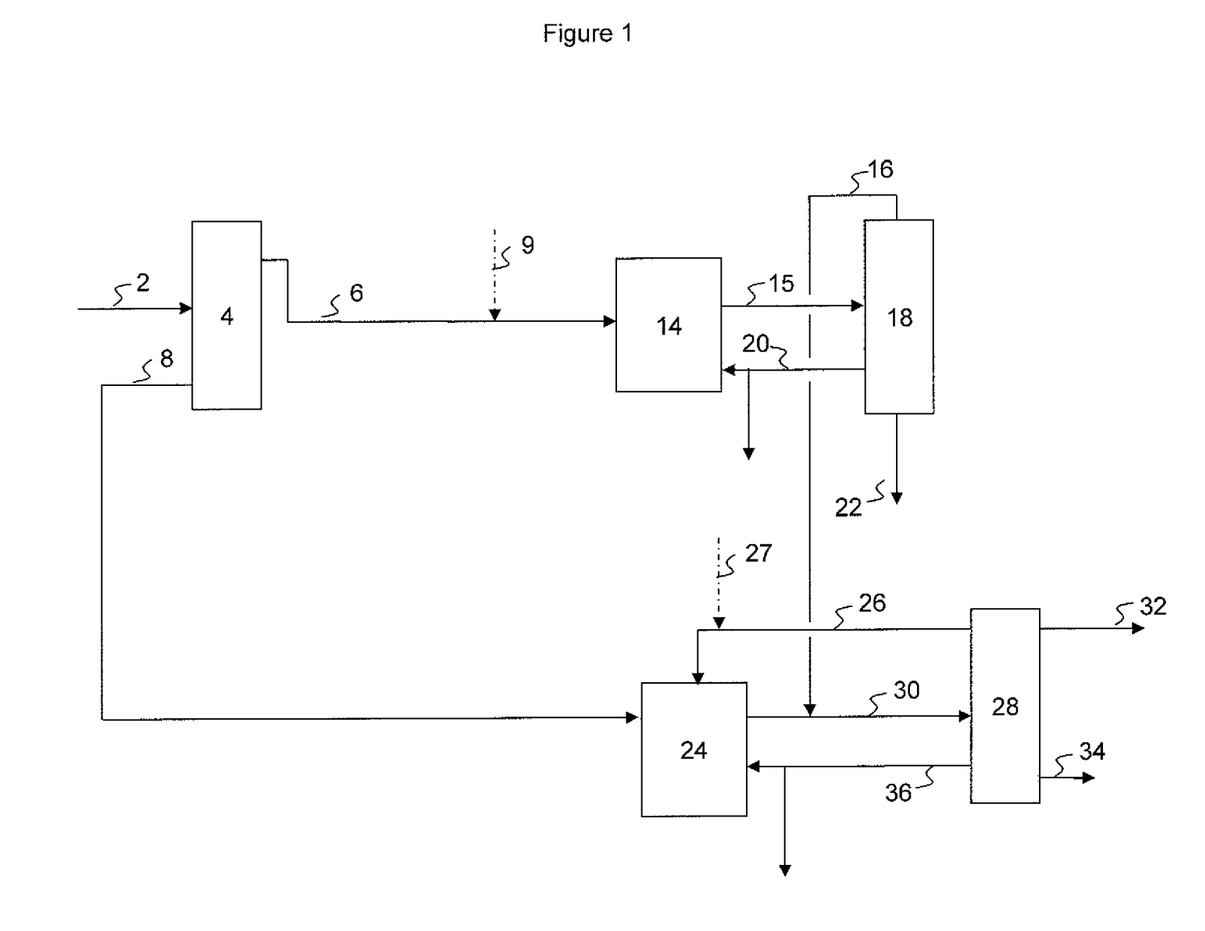
FIG. 1 is a simplified process flow diagram of a process for producing propylene according to embodiments disclosed herein.

Referring now to FIG. 1, a simplified process flow diagram of a process according to embodiments disclosed herein is illustrated. A $C_4$ cut, such as a Raffinate I stream containing isobutylene, 1-butene, and 2-butene may be fed via flow line 2 to a separation system 4, which may include one or more distillation columns and/or catalytic distillation reactor systems. The $C_4$ cut may then be fractionated to result in an isobutylene fraction, recovered via flow line 6, and a 2-butene fraction, recovered via flow line 8. Depending upon the separation requirements and equipment used in separation zone 4, the isobutylene fraction may include isobutylene, isobutane and/or 1-butene, as well as trace 2-butene.

The isobutylene fraction may then be fed to autometathesis reaction zone 14 containing a metathesis catalyst. If desired or available, a fresh isobutylene feed 9 may be combined with isobutylene fraction 6 to adjust a ratio of isobutylene to 1-butene and 2-butene in the system. The isobutylene may be brought into contact with the metathesis catalyst at appropriate operating conditions for conversion of at least a portion of the isobutylene to ethylene and 2,3-dimethyl-2-butene. When present, 1-butene may also react with itself or with isobutylene to produce ethylene via Reactions 3 and 7. Also, when trace 2-butene is present, ethylene may react with the 2-butene to produce some propylene. Other reactions may also be possible.

The autometathesis effluent may be recovered via flow line 15 and fed to a separation system 18, which may include a depropanizer, for example, for recovering a fraction comprising ethylene and propylene, and a debutanizer, for recovering a $C_4$ fraction (isobutylene, 1-butene, trace 2-butene, as well as isobutane, when present). Ethylene and propylene may be recovered from the depropanizer via flow line 16, the $C_4$ fraction may be recovered via flow line 20, and the $C_5$s and $C_6$s produced may be recovered via flow line 22.

The $C_4$ fraction may be recycled to metathesis reaction zone 14 via flow line 20, a portion of which may be purged, if necessary, to avoid buildup of isobutane within the system. The $C_5$s and $C_6$s recovered via flow line 22 may be used as a gasoline fraction, for example, or may be further processed to result in desired end products (such as production of ethylene and/or propylene via a cracking process (not shown)).

The ethylene and propylene fraction recovered via flow line 16 may be fed to separation zone 28, which may include a deethanizer, a depropanizer, and a debutanizer, for example. An ethylene fraction may be recovered from the deethanizer via flow stream 26, and the propylene may be recovered via flow stream 32.

The ethylene produced in metathesis reaction zone 14 and recovered in separation zones 18, 28 via flow stream 26 may then be combined with the 2-butene fraction in flow stream 8 and fed to conventional metathesis reaction zone 24 containing a metathesis catalyst. If desired and available, fresh ethylene may be fed to metathesis reaction zone 24 via flow line 27. The 2-butene and ethylene may then be brought into contact with the metathesis catalyst at appropriate operating conditions for conversion of at least a portion of the 2-butene and ethylene to form propylene.

The effluent from conventional metathesis reaction zone 24 may be recovered via flow stream 30, which may then be fed to separation zone 28 along with ethylene fraction 26 for separation of the metathesis products. As mentioned above, separation zone 28 may include a deethanizer, a depropanizer, and a debutanizer, for example. Unreacted ethylene in the conventional metathesis effluent and ethylene produced in automethathesis reaction zone 14 may be recovered from the deethanizer via flow line 26 for recycle/feed to conventional metatheses reaction zone 24. Propylene in both the conventional metathesis and autometathesis effluents may be recovered from the depropanizer via flow line 32. A $C_4$ fraction may be recovered from the debutanizer via flow line 36, including 2-butene, for recycle to conventional metathesis reaction zone 24. If necessary, a portion of the $C_4$ fraction may be purged to avoid buildup of n-butanes in the system. A $C_{5+}$ fraction may also be recovered from the debutanizer via flow line 34.

As mentioned above, it may be desired to adjust the relative amounts of isobutylene, 1-butene, and/or 2-butene in the system. For example, it may be desired to limit the amount of 1-butene in the isobutylene fraction. This may be accomplished, for example, by adjusting fractionation conditions in fractionation zone 4. Alternatively, the amount of 1-butene in the isobutylene fraction may be reduced by isomerizing the 1-butene to 2-butene prior to or during fractionation in separation zone 4. As another example, it may be desired to increase an amount of isobutylene while decreasing the amount of 1-butene in the isobutylene fraction, which may be accomplished via skeletal isomerization of 1-butene and/or 2-butene to form isobutylene. Isomerization catalysts and reaction conditions are disclosed in U.S. Pat. No. 5,087,780, for example. Skeletal isomerization catalysts and reaction conditions are disclosed in U.S. Pat. Nos. 4,410,753, 5,321,193, 5,321,194, 5,382,743, and 6,136,289, among others. Each of these patents is incorporated herein by reference.

Figure 2:
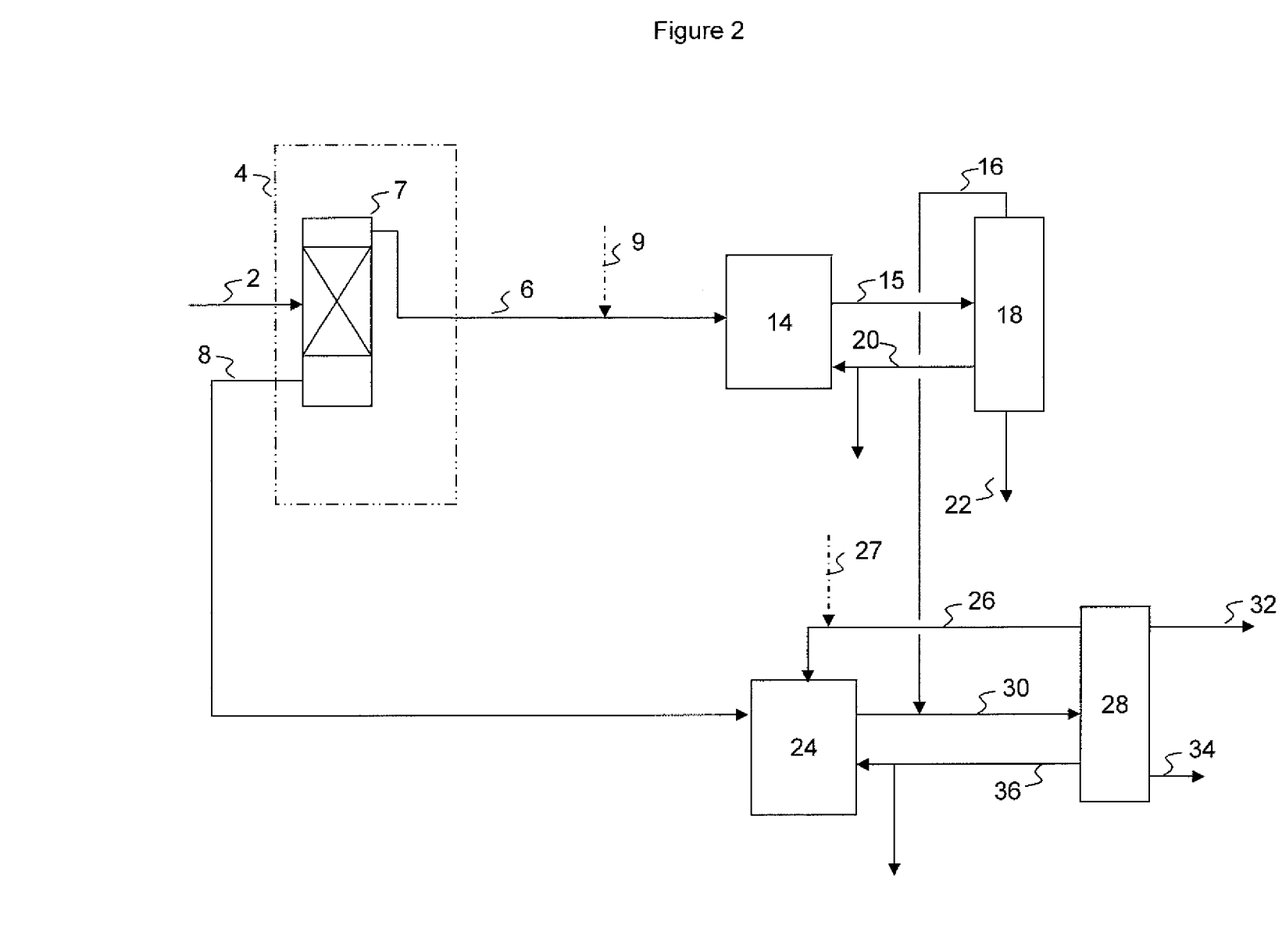
FIG. 2 is a simplified process flow diagram of a process for producing propylene according to embodiments disclosed herein.

Referring now to FIG. 2, a simplified process flow diagram for producing propylene according to embodiments disclosed herein is illustrated, where like numerals represent like parts. In this embodiment, separation zone 4 includes a catalytic distillation reaction zone 7, including an isomerization or a skeletal isomerization catalyst. Additionally or alternatively, a fixed bed isomerization reactor (not shown) may be used upstream of the catalytic distillation reaction zone 7.

Figure 3:
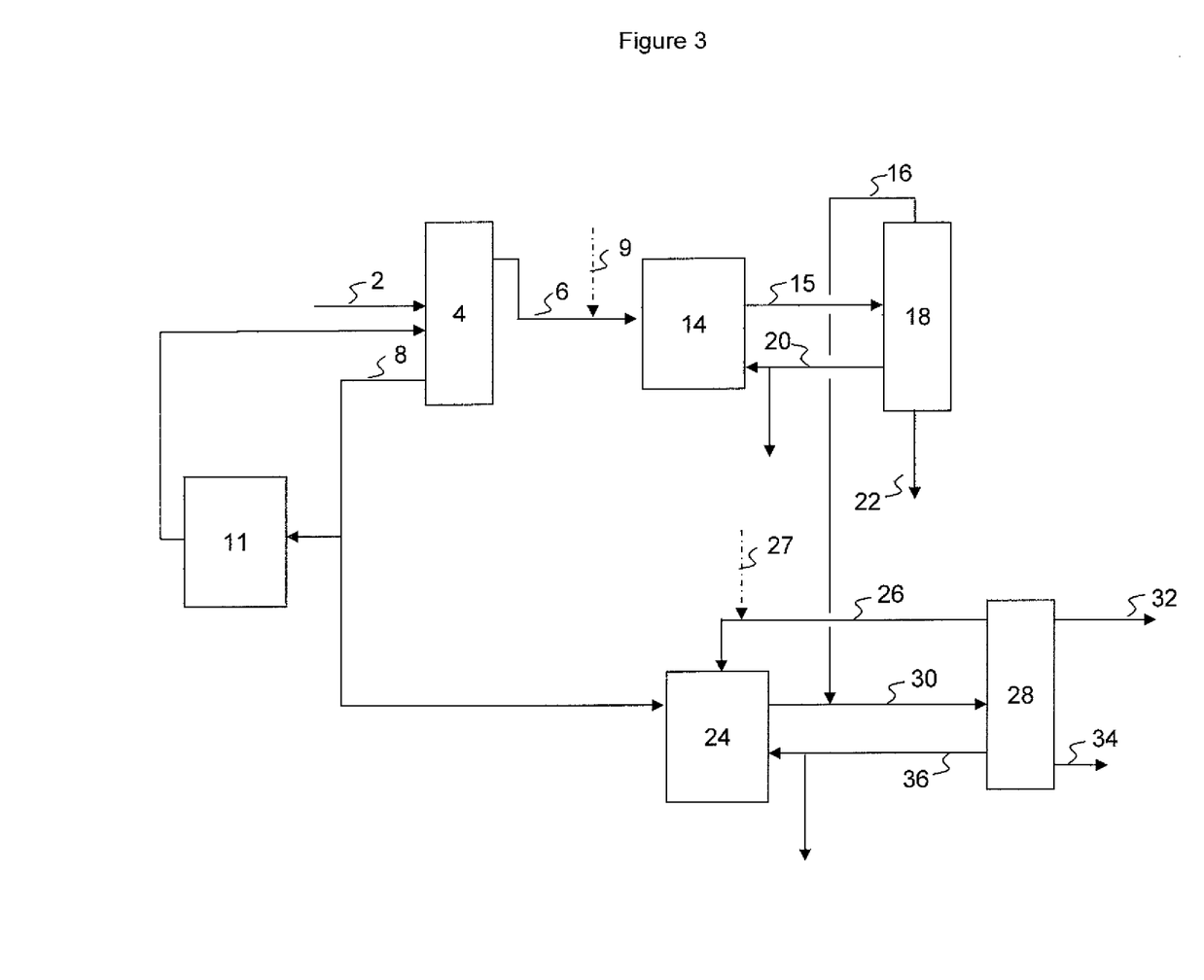
FIG. 3 is a simplified process flow diagram of a process for producing propylene according to embodiments disclosed herein.

Referring now to FIG. 3, a simplified process flow diagram for producing propylene according to embodiments disclosed herein is illustrated, where like numerals represent like parts. In this embodiment, an isomerization reaction zone 11 may be used to isomerize a portion of the 2-butene to form additional isobutylene and/or 1-butene.

Figure 4:
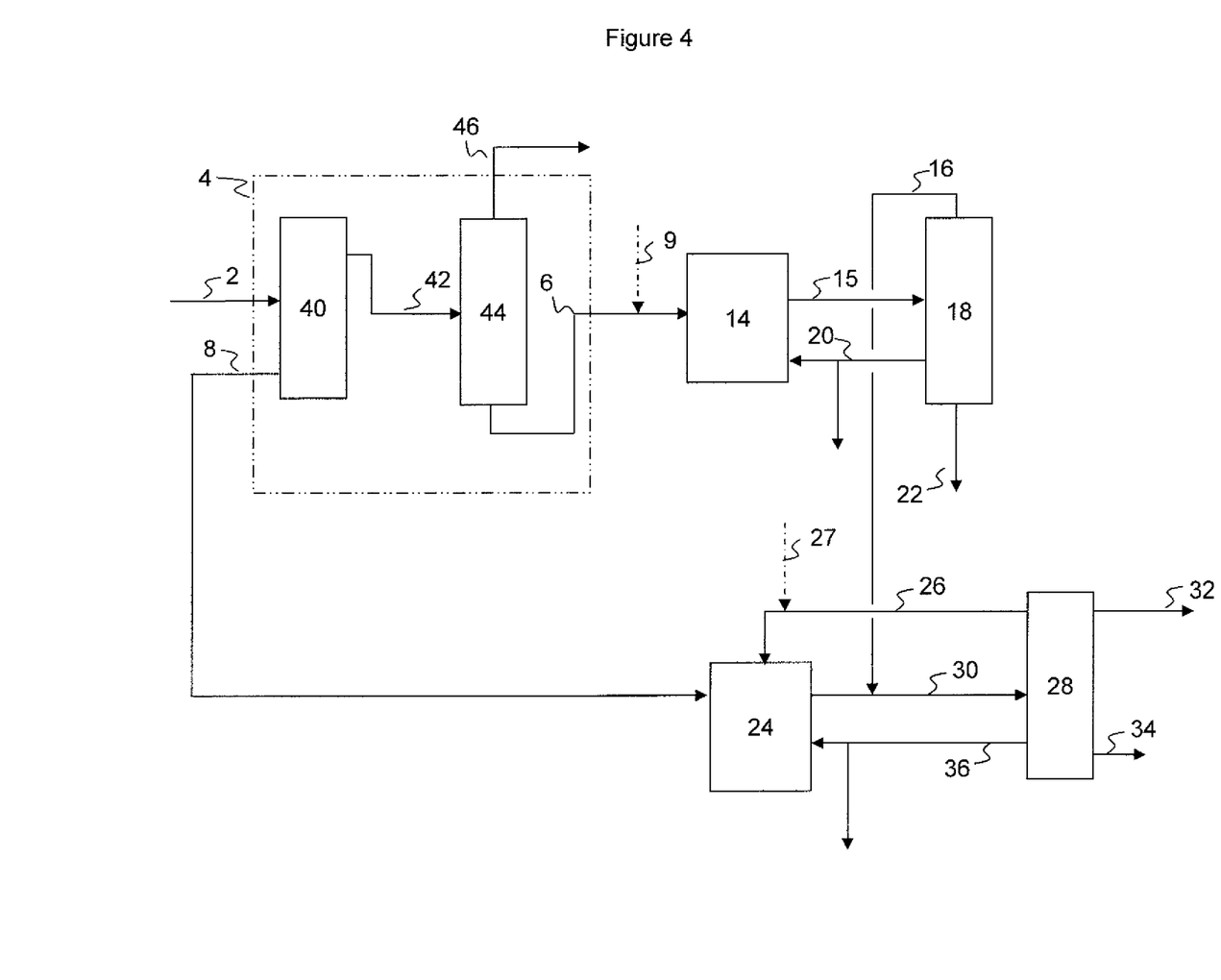
FIG. 4 is a simplified process flow diagram of a process for producing propylene according to embodiments disclosed herein.

Referring now to FIG. 4, a simplified process flow diagram for producing propylene according to embodiments disclosed herein is illustrated, where like numerals represent like parts. In this embodiment, separation zone 4 includes a deisobutylenizer 40 for separating 1-butene, isobutylene, and isobutane from 2-butene and n-butane, when present. The 2-butene fraction is recovered via flow stream 8, and processed as above. The overheads from deisobutylenizer 40 may be recovered via flow stream 42 and further fractionated in a deisobutanizer 44 to separate isobutane from the remaining olefins, isobutylene and 1-butene, if present. The isobutane may be recovered via flow stream 46. The isobutylene fraction may be recovered via flow line 6 and processed as described above. Use of a deisobutanizer 44 may provide for a more concentrated olefin stream 6 fed to autometathesis reactor 14, as well as for decreased separation and purge rates for downstream processes.

Figure 5:
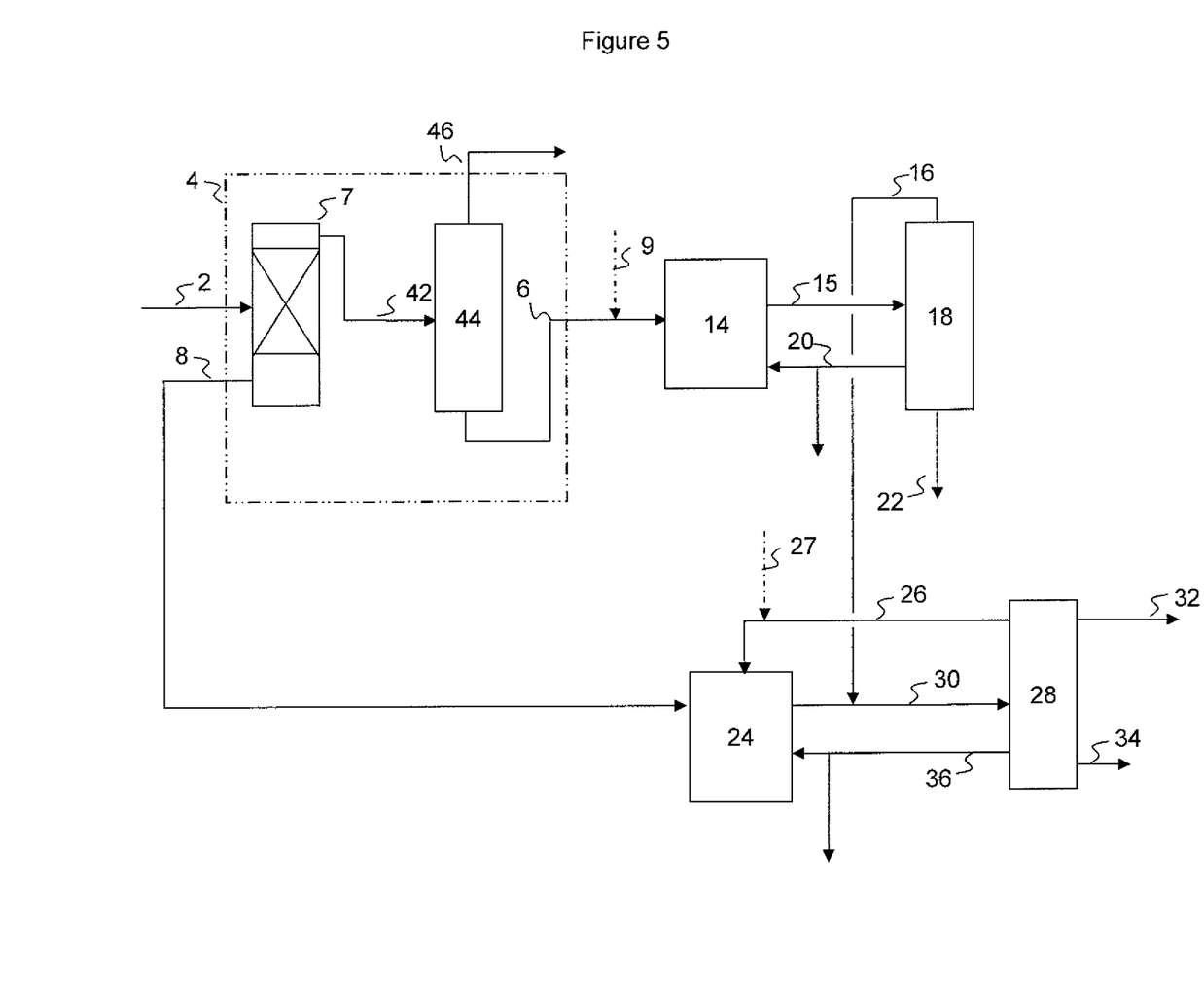
FIG. 5 is a simplified process flow diagram of a process for producing propylene according to embodiments disclosed herein.

Referring now to FIG. 5, a simplified process flow diagram for producing propylene according to embodiments disclosed herein is illustrated, where like numerals represent like parts. In this embodiment, fractionation zone 4 includes a catalytic distillation reactor system 7 and a deisobutanizer 44.

Figure 6:
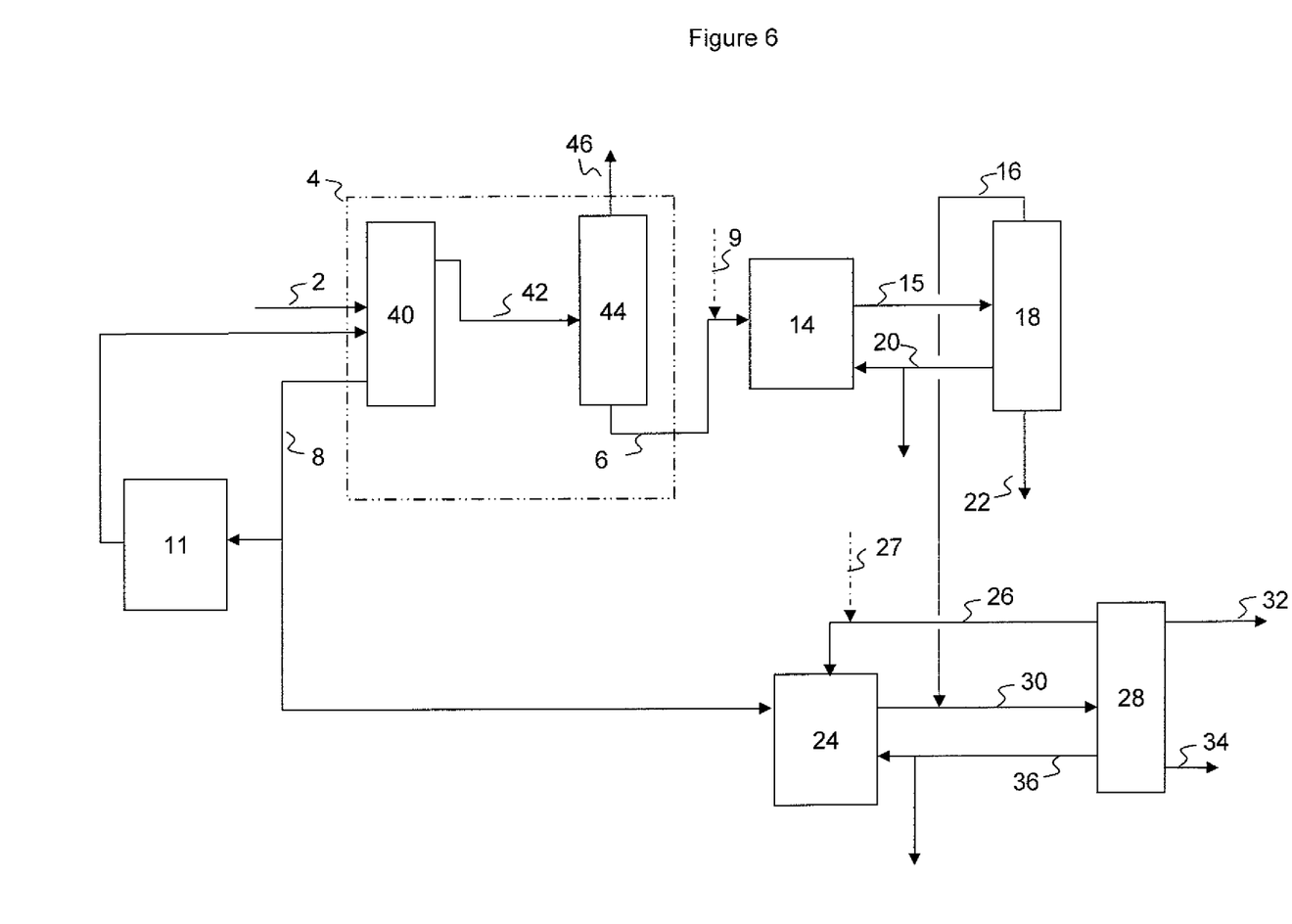
FIG. 6 is a simplified process flow diagram of a process for producing propylene according to embodiments disclosed herein.

Referring now to FIG. 6, a simplified process flow diagram for producing propylene according to embodiments disclosed herein is illustrated, where like numerals represent like parts. In this embodiment, separation zone 4 includes a deisobutylenizer 40 and a deisobutanizer 44, as well as an isomerization reaction zone 11.

While only a limited number of possible flow, reaction, and separation schemes have been illustrated, one skilled in the art would appreciate that other schemes are possible to similarly produce propylene via metathesis of a $C_4$ stream with use of little or no ethylene. The particular flow, reaction, or separation scheme used may depend on the feeds available, such as the relative quantities of isobutane, isobutylene, 1-butene, and 2-butene.

In the above embodiments, the autometathesis and conventional metathesis reactors may be operated at a pressure between 2 and 40 atmospheres in some embodiments, and between 5 and 15 atmospheres in other embodiments. The metathesis reactors may be operated such that the reaction temperature is within the range from about 50° C. to about 600° C.; within the range from about 200° C. to about 450° C. in other embodiments; and from about 250° C. to about 400° C. in yet other embodiments. The metathesis reactions may be performed at a weight hourly space velocity (WHSV) in the range from about 3 to about 200 in some embodiments, and from about 6 to about 40 in other embodiments.

The reactions may be carried out by contacting the olefin(s) with the respective metathesis catalysts in the liquid phase or the gas phase, depending on structure and molecular weight of the olefin(s). If the reaction is carried out in the liquid phase, solvents or diluents for the reaction can be used. Aliphatic saturated hydrocarbons, e.g., pentanes, hexanes, cyclohexanes, dodecanes and aromatic hydrocarbons such as benzene and toluene are suitable. If the reaction is carried out in the gaseous phase, diluents such as saturated aliphatic hydrocarbons, for example, methane, ethane, and/or substantially inert gases, such as nitrogen and argon, may be present. For high product yield, the reaction may be conducted in the absence of significant amounts of deactivating materials such as water and oxygen.

The contact time needed to obtain a desirable yield of metathesis reaction products depends upon several factors, such as the activity of the catalyst, temperature, pressure, and the structure of the olefin(s) to be metathesized. Length of time during which the olefin(s) are contacted with catalyst can conveniently vary between 0.1 seconds and 4 hours, preferably from about 0.5 sec to about 0.5 hrs. The metathesis reactions may be conducted batch-wise or continuously with fixed catalyst beds, slurried catalyst, fluidized beds, or by using any other conventional contacting techniques.

The catalyst contained within the metathesis reactors may be any known autometathesis or conventional metathesis catalysts, which may be the same or different, and may include oxides of Group VIA and Group VIIA metals on supports. Catalyst supports can be of any type and could include alumina, silica, mixtures thereof, zirconia, and zeolites. In addition to the metathesis catalyst, the catalyst contained in the metathesis reactor may include a double bond isomerization catalyst such as magnesium oxide or calcium oxide. In some embodiments, the catalyst may include a promoter to reduce acidity; for example, an alkali metal (sodium, potassium or lithium), cesium, a rare earth, etc.

The above described processes provide for the efficient production of propylene from C4 olefins. Processes disclosed herein may be advantageously employed where there is no or little ethylene available, or where there is excess C4 olefins relative to the available ethylene.

EXAMPLES

The following examples are derived from modeling techniques. Although the work has been performed, these examples are presented in the present tense to comply with applicable rules.

Figure 7:
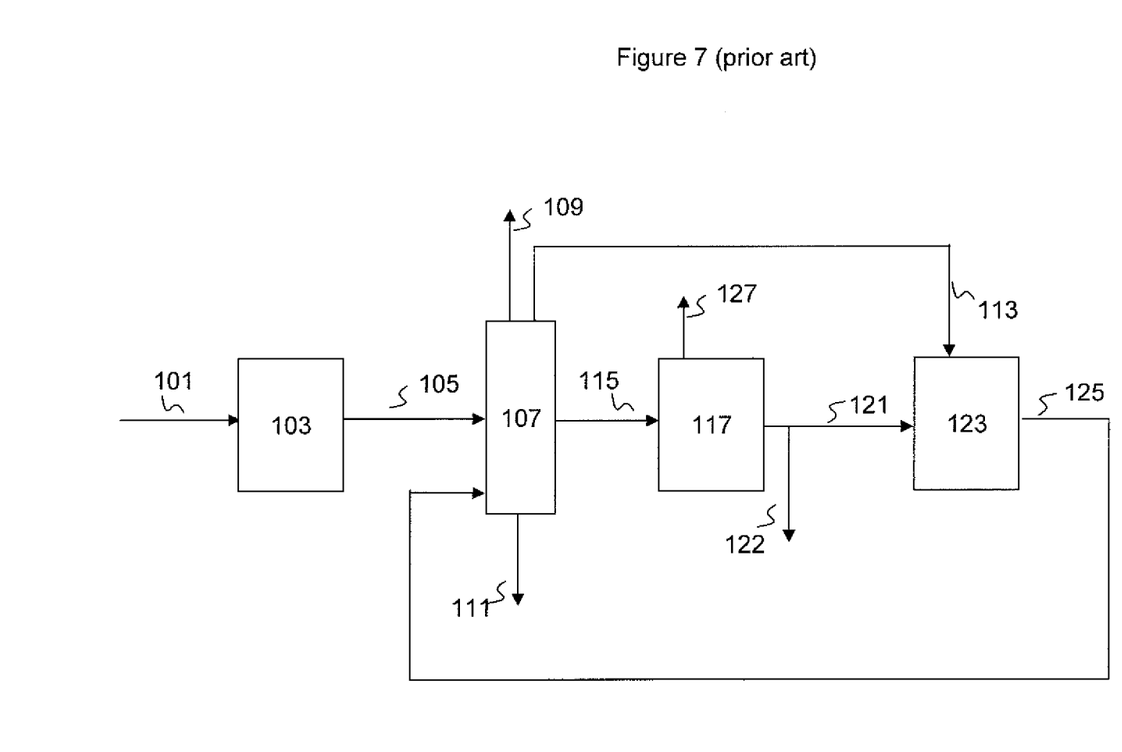
FIG. 7 is a simplified process flow diagram of a comparative process for producing propylene.

In the following Examples and Comparative Examples, the process for producing propylene according to embodiments disclosed herein is compared to the process as disclosed U.S. Pat. No. 7,214,841 ('841). A simplified process flow diagram of the process as disclosed in the '841 patent is illustrated in FIG. 7. In this process, the entire $C_4$ cut (Raffinate I) is fed via flow line 101 to autometathesis reactor 103. The effluent from autometathesis reactor 103 is recovered via flow line 105 and fed to separation zone 107, for recovery of a propylene fraction 109, a $C_5/C_6$ fraction 111, an ethylene fraction 113, and a $C_4$ fraction 115, which includes 1-butene, 2-butene, etc. The $C_4$ fraction in flow line 115 is then fed to catalytic distillation reactor 117 for concurrent isomerization of the 1-butene to form additional 2-butene and separation of the 2-butene from isobutylene. The 2-butene fraction is recovered via flow line 121, and the isobutylene fraction may be recovered via flow line 127. The 2-butene fraction 121 and ethylene fraction 113 are then contacted with a metathesis catalyst in conventional metathesis reaction zone 123. The effluent from reaction zone 123 may be recovered via flow line 125 and fed to separation zone 107 for separation and recovery of the respective fractions. To avoid buildup of n-butanes, for example, a $C_4$ purge may be taken via flow line 122.

Comparative Example 1

The process as illustrated in FIG. 7 is simulated. The details and results of the simulation are given in Tables 2 and 4. The stream numbers in Table 2 correspond to those shown in FIG. 7. The feed 101 to the process includes a total flow of isobutylene of 142 kilotons per year (kta), 1-butene of 178 kta, and 2-butene of 357 kta for a total olefin flow of 677 kta. The isobutylene to n-butenes ratio in the feed is approximately 0.26. There are a total of 4 fractionation towers.

TABLE 2

| | Stream # | | | | | | |
|---|---|---|---|---|---|---|---|
| | 101 | 105 | 113 | 109 | 111 | 127 | 122 |
| Ethylene | 0.0 | 1.2 | 98.5 | 0.0 | 0.0 | 0.0 | 0.0 |
| Propene | 0.0 | 11.5 | 1.5 | 99.9 | 0.0 | 0.6 | 0.0 |
| Iso-Butane | 32.6 | 32.6 | 0.0 | 0.0 | 0.1 | 84.9 | 1.6 |
| n-Butane | 7.9 | 7.9 | 0.0 | 0.0 | 2.6 | 3.1 | 59.4 |
| Tr2-Butene | 18.8 | 11.1 | 0.0 | 0.0 | 0.8 | 1.0 | 24.4 |
| 1-Butene | 15.6 | 3.2 | 0.0 | 0.0 | 0.1 | 0.2 | 0.0 |
| Iso-Butene | 12.5 | 4.7 | 0.0 | 0.0 | 0.0 | 10.2 | 1.3 |
| Cis2-Butene | 12.6 | 7.4 | 0.0 | 0.0 | 1.0 | 0.0 | 11.3 |
| n-C5 | 0.0 | 8.3 | 0.0 | 0.0 | 42.0 | 0.0 | 1.4 |
| I-C5 | 0.0 | 4.6 | 0.0 | 0.0 | 15.7 | 0.0 | 0.4 |
| n-C6 | 0.0 | 1.8 | 0.0 | 0.0 | 15.0 | 0.0 | 0.0 |
| I-C6 | 0.0 | 5.5 | 0.0 | 0.0 | 21.3 | 0.0 | 0.0 |
| C6+ | 0.0 | 0.0 | 0.0 | 0.0 | 1.4 | 0.0 | 0.0 |
| Flow, KTA | 1138 | 1138 | 33 | 250 | 343 | 432 | 112 |

The simulation is performed to meet various convergence criteria, and the "steady state" simulation results indicate the following. The ethylene to butene feed ratio to the conventional metathesis reactor is 0.18. Analysis of the product flow streams indicates $nC_4$ utilization is approximately 90.4%; $iC_4$ utilization is approximately 67.8%; and the overall olefin utilization is approximately 85.8% to both propylene and gasoline range olefins. C3 production as a percentage of total olefin feed is approximately 36.9%. The isopentenes and isohexenes total flow is 127 kta and the normal pentenes and normal hexenes is 196 kta for an $iC_{5-6}$ to $nC_{5-6}$ ratio of 60.5%, indicating the extent of reactions 2 and 3 forming normal $C_{5-6}$ olefins.

Comparative Example 2

Comparative Example 2 is also based on FIG. 1, with increased isobutane concentration requirement in the overheads of tower 117 (retention of more olefins in stream 121). The feed to the process is the same as that used in Comparative Example 1, having an isobutylene to n-butenes ratio of 0.26. The details and results of the simulation are given in Tables 3 and 4.

TABLE 3

| | Stream # | | | | | | |
|---|---|---|---|---|---|---|---|
| | 101 | 105 | 113 | 109 | 111 | 127 | 122 |
| Ethylene | 0.0 | 1.2 | 98.5 | 0.0 | 0.0 | 0.0 | 0.0 |
| Propene | 0.0 | 11.5 | 1.5 | 99.9 | 0.0 | 0.7 | 0.0 |
| Iso-Butane | 32.6 | 32.6 | 0.0 | 0.0 | 0.1 | 95.4 | 3.9 |
| n-Butane | 7.9 | 7.9 | 0.0 | 0.0 | 3.0 | 0.0 | 59.2 |
| Tr2-Butene | 18.8 | 11.1 | 0.0 | 0.0 | 0.8 | 0.0 | 20.9 |
| 1-Butene | 15.6 | 3.2 | 0.0 | 0.0 | 0.1 | 0.0 | 0.1 |
| Iso-Butene | 12.5 | 4.7 | 0.0 | 0.0 | 0.0 | 3.9 | 4.6 |
| Cis2-Butene | 12.6 | 7.4 | 0.0 | 0.0 | 1.0 | 0.0 | 9.5 |
| n-C5 | 0.0 | 8.3 | 0.0 | 0.0 | 37.3 | 0.0 | 1.3 |
| I-C5 | 0.0 | 4.6 | 0.0 | 0.0 | 18.2 | 0.0 | 0.5 |
| n-C6 | 0.0 | 1.8 | 0.0 | 0.0 | 12.3 | 0.0 | 0.0 |
| I-C6 | 0.0 | 5.5 | 0.0 | 0.0 | 26.3 | 0.0 | 0.0 |
| C6+ | 0.0 | 0.0 | 0.0 | 0.0 | 0.9 | 0.0 | 0.0 |
| Flow, KTA | 1138 | 1138 | 38 | 264 | 360 | 352 | 132 |

The simulation is performed to meet various convergence criteria, and the "steady state" simulation results indicate the following. The ethylene to butene feed ratio to the conventional metathesis reactor is 0.2. Analysis of the product flow streams indicates $nC_4$ utilization is approximately 91.2%; $iC_4$ utilization is approximately 85.1%; and the overall olefin utilization is approximately 90.2% to both propylene and gasoline range olefins. C3 production as a percentage of total olefin feed is approximately 38.9%. The isopentenes and isohexenes total flow is 160 kta and the normal pentenes and normal hexenes is 179 kta for an $iC_{5-6}$ to $nC_{5-6}$ ratio of 52.8%, indicating the extent of reactions 2 and 3 forming normal $C_{5-6}$ olefins.

As compared to Comparative Example 1, increasing the amount of isobutylene in the bottoms of tower 117 improves the overall utilization of olefins and the yield of propylene, but requires increased utilities (Q=heat duty, in megawatts (MW) for the condenser (c) and reboiler (r)) to perform the required separations.

TABLE 4

| Fractionation Tower | Comp. Ex. 1 | Comp. Ex. 2 |
|---|---|---|
| Deethanizer | | |
| Stages | 33 | 33 |
| Qc (MW) | 1.11 | 1.26 |
| Qr (MW) | 18.2 | 17.7 |
| Overhead Specification | 1% $C_3$ | 1% $C_3$ |
| Bottoms Specification | 0.01% $C_2$ | 0.01% $C_2$ |
| Depropanizer | | |
| Stages | 40 | 40 |
| Qc (MW) | 23.5 | 25.5 |
| Qr (MW) | 24.9 | 27.0 |
| Overhead Specification | 99.99% $C_3$ | 99.99% $C_3$ |
| Bottoms Specification | 0.018% $C_3$ | 0.018% $C_3$ |
| Debutanizer | | |
| Stages | 20 | 20 |
| Qc (MW) | 30.4 | 32.5 |
| Qr (MW) | 23.8 | 26.3 |
| Overhead Specification | 0.5% $C_5$ | 0.5% $C_5$ |
| Bottoms Specification | 1% $C_4$ | 1% $C_4$ |

TABLE 4-continued

| Fractionation Tower | Comp. Ex. 1 | Comp. Ex. 2 |
|---|---|---|
| Deisobutanizer | | |
| Stages | 60 | 70 |
| Qc (MW) | 71.7 | 166.3 |
| Qr (MW) | 63.9 | 159.2 |
| Overhead Specification | 1% $nC_4$ | 4% isobutene |
| Bottoms Specification | 3% isobutane + isobutylene | Reflux ratio = 14 |
| Total Utility | | |
| Qc (MW) | 126.7 | 225.6 |
| Qr (MW) | 125.8 | 229.2 |

Example 1

A process similar to that illustrated in FIG. 4 is simulated, with separation zone 4 including a deisobutylenizer 40 and a deisobutanizer 44. The details and results of the simulation are given in Tables 5 and 7. The stream numbers in Table 5 correspond to those shown in FIG. 4. The feed to the system (streams 2 and 9) includes a total flow of isobutylene of 251 kilotons per year (kta)(78+173), 1-butene of 97 kta, and 2-butene of 196 kta for a total olefin flow of 371 kta. The isobutylene to n-butenes ratio in feed 2 is approximately 0.26. There are a total of 6 fractionation towers.

TABLE 5

| | Stream # | | | | | | | | | |
|---|---|---|---|---|---|---|---|---|---|---|
| | 2 | 8 | 46 | 6 | 9 | 16 | 22 | 30 | 32 | 34 |
| Ethylene | 0.0 | 0.0 | 0.0 | 0.0 | 0.0 | 89.1 | 0.0 | 20.1 | 0.0 | 0.0 |
| Propene | 0.0 | 0.0 | 0.0 | 0.0 | 0.0 | 6.2 | 0.0 | 34.1 | 98.7 | 0.0 |
| Iso-Butane | 32.6 | 0.0 | 95.2 | 5.2 | 0.0 | 2.8 | 0.0 | 1.4 | 0.1 | 0.0 |
| n-Butane | 7.9 | 19.2 | 0.0 | 1.6 | 0.0 | 0.1 | 0.0 | 30.0 | 0.7 | 12.3 |
| Tr2-Butene | 18.8 | 47.3 | 0.0 | 2.0 | 0.0 | 0.0 | 0.0 | 5.9 | 0.1 | 2.5 |
| 1-Butene | 15.6 | 0.7 | 0.4 | 53.1 | 0.0 | 0.1 | 0.0 | 2.4 | 0.3 | 0.1 |
| Iso-Butene | 12.5 | 0.3 | 4.4 | 38.0 | 100 | 1.8 | 0.0 | 0.5 | 0.1 | 0.0 |
| Cis2-Butene | 12.6 | 32.5 | 0.0 | 0.1 | 0.0 | 0.0 | 0.0 | 3.9 | 0.0 | 4.5 |
| n-C5 | 0.0 | 0.0 | 0.0 | 0.0 | 0.0 | 0.0 | 0.0 | 1.3 | 0.0 | 63.3 |
| I-C5 | 0.0 | 0.0 | 0.0 | 0.0 | 0.0 | 0.0 | 0.1 | 0.1 | 0.0 | 6.3 |
| n-C6 | 0.0 | 0.0 | 0.0 | 0.0 | 0.0 | 0.0 | 2.2 | 0.2 | 0.0 | 7.8 |
| I-C6 | 0.0 | 0.0 | 0.0 | 0.0 | 0.0 | 0.0 | 97.7 | 0.1 | 0.0 | 2.9 |
| C6+ | 0.0 | 0.0 | 0.0 | 0.0 | 0.0 | 0.0 | 0.0 | 0.0 | 0.0 | 0.3 |
| Flow, KTA | 624 | 241 | 204 | 179 | 173 | 88 | 241 | 722 | 251 | 15 |

The simulation is performed to meet various convergence criteria, and the "steady state" simulation results indicate the following. The ethylene to butene feed ratio to the conventional metathesis reactor is 1.7. Analysis of the product flow streams indicates $nC_4$ utilization is approximately 93%; $iC_4$ utilization is approximately 91.4%; and the overall olefin utilization is approximately 92.8% to both propylene and gasoline range olefins. C3 production as a percentage of total olefin feed is approximately 46.1%. The isopentenes and isohexenes total flow is 235 kta and the normal pentenes and normal hexenes is 6 kta for an $iC_{5-6}$ to $nC_{5-6}$ ratio of 2.5%. This process results in a very high efficiency of normal $C_4$ olefins to propylene, and the olefin utilizations are high.

Example 2

A process similar to that illustrated in FIG. 5 is simulated, with separation zone 4 including a catalytic distillation reactor system 7 (concurrent isomerization+fractionation in a deisobutylenizer) and a deisobutanizer 44. The details and results of the simulation are given in Tables 6 and 7. The stream numbers in Table 6 correspond to those shown in FIG. 5. The feed to the system (streams 2 and 9) includes a total flow of isobutylene of 344 kilotons per year (kta)(53+290), 1-butene of 68 kta, and 2-butene of 135 kta for a total olefin flow of 546 kta. The isobutylene to n-butenes ratio in feed 2 is approximately 0.26. There are a total of 6 fractionation towers.

TABLE 6

| | Stream # | | | | | | | | | |
|---|---|---|---|---|---|---|---|---|---|---|
| | 2 | 8 | 46 | 6 | 9 | 16 | 22 | 30 | 32 | 34 |
| Ethylene | 0.0 | 0.0 | 0.0 | 0.0 | 0.0 | 89.1 | 0.0 | 20.1 | 0.0 | 0.0 |
| Propene | 0.0 | 0.0 | 0.0 | 0.0 | 0.0 | 6.2 | 0.0 | 34.1 | 98.7 | 0.0 |
| Iso-Butane | 32.6 | 0.0 | 95.2 | 5.2 | 0.0 | 2.8 | 0.0 | 1.4 | 0.1 | 0.0 |
| n-Butane | 7.9 | 19.2 | 0.0 | 1.6 | 0.0 | 0.1 | 0.0 | 30.0 | 0.7 | 12.3 |
| Tr2-Butene | 18.8 | 47.3 | 0.0 | 2.0 | 0.0 | 0.0 | 0.0 | 5.9 | 0.1 | 2.5 |
| 1-Butene | 15.6 | 0.7 | 0.4 | 53.1 | 0.0 | 0.1 | 0.0 | 2.4 | 0.3 | 0.1 |
| Iso-Butene | 12.5 | 0.3 | 4.4 | 38.0 | 100 | 1.8 | 0.0 | 0.5 | 0.1 | 0.0 |
| Cis2-Butene | 12.6 | 32.5 | 0.0 | 0.1 | 0.0 | 0.0 | 0.0 | 3.9 | 0.0 | 4.5 |
| n-C5 | 0.0 | 0.0 | 0.0 | 0.0 | 0.0 | 0.0 | 0.0 | 1.3 | 0.0 | 63.3 |
| I-C5 | 0.0 | 0.0 | 0.0 | 0.0 | 0.0 | 0.0 | 0.1 | 0.1 | 0.0 | 6.3 |
| n-C6 | 0.0 | 0.0 | 0.0 | 0.0 | 0.0 | 0.0 | 2.2 | 0.2 | 0.0 | 7.8 |
| I-C6 | 0.0 | 0.0 | 0.0 | 0.0 | 0.0 | 0.0 | 97.7 | 0.1 | 0.0 | 2.9 |
| C6+ | 0.0 | 0.0 | 0.0 | 0.0 | 0.0 | 0.0 | 0.0 | 0.0 | 0.0 | 0.3 |
| Flow, KTA | 624 | 241 | 204 | 179 | 173 | 88 | 241 | 722 | 251 | 15 |

The simulation is performed to meet various convergence criteria, and the "steady state" simulation results indicate the following. The ethylene to butene feed ratio to the conventional metathesis reactor is 1.7. Analysis of the product flow streams indicates $nC_4$ utilization is approximately 90.7%; $iC_4$ utilization is approximately 94.9%; and the overall olefin utilization is approximately 93.3% to both propylene and gasoline range olefins. C3 production as a percentage of total olefin feed is approximately 45.9%. This process results in a very high efficiency of normal $C_4$ olefins to propylene, and the olefin utilizations are high.

TABLE 7

| Fractionation Tower | Example 1 | Example 2 |
|---|---|---|
| Deethanizer (28) | | |
| Stages | 33 | 33 |
| Qc (MW) | 5.51 | 6.0 |
| Qr (MW) | 4.81 | 4.52 |
| Overhead Specification | 1% $C_3$ | 1% $C_3$ |
| Bottoms Specification | 0.01% $C_2$ | 0.01% $C_2$ |
| Depropanizer (28) | | |
| Stages | 40 | 40 |
| Qc (MW) | 7.4 | 5.9 |
| Qr (MW) | 8.1 | 7.5 |
| Overhead Specification | 99.99% $C_3$ | 99.99% $C_3$ |
| Bottoms Specification | 0.018% $C_3$ | 0.018% $C_3$ |
| Deisobutylenizer (40, 7) | | |
| Stages | 60 | 60 |
| Qc (MW) | 58.4 | 30.4 |
| Qr (MW) | 57.6 | 24.5 |
| Overhead Specification | 1% 2-butene | 1% 2-butene |
| Bottoms Specification | 1% 1-butene + isobutylene | 1% 1-butene + isobutylene |
| Deisobutanizer (44) | | |
| Stages | 100 | 100 |
| Qc (MW) | 90.3 | 60.6 |
| Qr (MW) | 90.3 | 60.6 |
| Overhead Specification | 5% 1-butene + isobutylene | 5% 1-butene + isobutylene |
| Bottoms Specification | 5% isobutane | 5% isobutane |
| Depropanizer (18) | | |
| Stages | 33 | 33 |
| Qc (MW) | 7.37 | 4.95 |
| Qr (MW) | 14.8 | 12.2 |
| Overhead Specification | 1% $C_4$ | 1% $C_4$ |
| Bottoms Specification | 0.1% $C_3$ | 0.1% $C_3$ |
| Debutanizer (18) | | |
| Stages | 20 | 20 |
| Qc (MW) | 15.6 | 14.5 |
| Qr (MW) | 11.7 | 10.8 |
| Overhead Specification | 1% $C_6$ | 1% $C_6$ |
| Bottoms Specification | 0.1% $C_5$ | 0.1% $C_5$ |
| Total Utility | | |
| Qc (MW) | 184.5 | 123,3 |
| Qr (MW) | 187.3 | 120.1 |

As shown by the Examples above, embodiments disclosed herein provide an efficient process for the conversion of $C_4$ olefins to propylene.

As described above, embodiments disclosed herein provide for the production of propylene from $C_4$ olefins where there is no or little fresh ethylene, or an excess of $C_4$ olefins relative to available ethylene. Comparatively, embodiments disclosed herein may produce propylene at a very high utilization of $C_4$ olefins to propylene. In some embodiments, where 1-butene is converted to 2-butene, for example, processes according to embodiments disclosed herein may produce propylene at percentage yields approaching that of the theoretical amount of propylene from $nC_4$s in a conventional metathesis (with ethylene) process.

While possibly requiring additional capital equipment and utilities, namely additional fractionation towers as compared to the process in the Comparative Examples (6 towers vs. 4 towers in the Comparative Examples), the higher selectivity toward propylene provided by processes disclosed herein may offset the higher capital and operating expense. As such, embodiments disclosed herein provide a novel alternative process for producing propylene from $C_4$ olefins where there is no or little fresh ethylene, or an excess of $C_4$ olefins relative to available ethylene.

While the disclosure includes a limited number of embodiments, those skilled in the art, having benefit of this disclosure, will appreciate that other embodiments may be devised which do not depart from the scope of the present disclosure. Accordingly, the scope should be limited only by the attached claims.

What is claimed:

1. A process for the production of propylene from a mixed C4 hydrocarbon stream comprising isobutene, 1-butene, and 2-butene, the process comprising:
   concurrently:
      fractionating the mixed C4 hydrocarbon stream and isomerizing a portion of the 2-butene to form 1-butene to recover a first fraction comprising isobutene and 1-butene and a second fraction comprising 2-butene;
   contacting at least a portion of the first fraction with a first metathesis catalyst in a first metathesis reaction zone;
   recovering an effluent from the first metathesis reaction zone comprising at least one of ethylene, propylene, unreacted isobutene, C5 olefins, and C6 olefins;
   contacting at least a portion of the second fraction and ethylene with a second metathesis catalyst in a second metathesis reaction zone;
   recovering an effluent from the second reaction zone comprising at least one of unreacted ethylene, propylene, unreacted 2-butene,
   fractionating the effluent from the first metathesis reaction zone and the effluent from the second metathesis reaction zone to recover an ethylene fraction, a propylene fraction, one or more C4 fractions, and a fraction comprising at least one of C5 and C6 olefins.

2. The process of claim 1, further comprising feeding the ethylene fraction to the second metathesis reaction zone as the at least a portion of the ethylene in the effluent from the first metathesis reaction zone.

3. The process of claim 1, further comprising recycling the one or more C4 fractions to at least one of the first metathesis reaction zone and the second metathesis reaction zone.

4. The process of claim 1, wherein the first fraction further comprises isobutane, the process further comprising:
   fractionating the first fraction to recover an isobutane fraction and a fraction comprising isobutene and 1-butene; and
   feeding the fraction comprising isobutene and 1-butene to the first metathesis reaction zone as the at least a portion of the first fraction.

5. A process for the production of propylene, comprising:
   fractionating a mixed C4 hydrocarbon stream to recover a first fraction comprising isobutene and 1-butene and a second fraction comprising 2-butene;
   feeding a portion of the second fraction to an isomerization reaction zone containing an isomerization catalyst;

contacting the 2-butene with the isomerization catalyst to convert at least a portion of the 2-butene to 1-butene;
recovering an effluent from the isomerization reaction zone comprising the 1-butene and any unreacted 2-butene; and
feeding the effluent from the isomerization reaction zone to the fractionating a mixed C4 stream;
contacting at least a portion of the first fraction with a first metathesis catalyst in a first metathesis reaction zone;
recovering an effluent from the first metathesis reaction zone comprising at least one of ethylene, propylene, unreacted isobutene, unreacted 1-butene, C5 olefins, and C6 olefins;
fractionating the effluent from the first metathesis reaction zone to recover a fraction comprising ethylene and propylene, a fraction comprising any unreacted isobutene and any unreacted 1-butene, and a fraction comprising any C5 and C6 olefins;
contacting a remaining portion of the second fraction and ethylene with a second metathesis catalyst in a second metathesis reaction zone;
recovering an effluent from the second metathesis reaction zone comprising at least one of unreacted ethylene, propylene, and unreacted 2-butene,
fractionating the effluent from the second metathesis reaction zone and the fraction comprising ethylene and propylene to recover an ethylene fraction, a propylene fraction, a C4 fraction, and a fraction comprising at least one of C5 and C6 olefins;
feeding at least a portion of the ethylene fraction to the second metathesis reaction zone as the ethylene;
feeding at least a portion of the C4 fraction to the second metathesis reaction zone; and
feeding at least a portion of the fraction comprising any unreacted isobutene and any unreacted 1-butene to the first metathesis reaction zone.

6. The process of claim 5, wherein the first fraction further comprises isobutane, the process further comprising:
fractionating the first fraction to recover an isobutane fraction and a fraction comprising isobutene and 1-butene; and
feeding the fraction comprising isobutene and 1-butene to the first metathesis reaction zone as the at least a portion of the first fraction.

7. A process for the production of propylene, comprising:
feeding a mixed C4 hydrocarbon stream comprising 1-butene, 2-butene, and isobutene to a catalytic distillation reactor system;
concurrently in the catalytic distillation reactor system:
isomerizing at least a portion of the 2-butene to form 1-butene;
fractionating the mixed C4 hydrocarbon stream to recover a first fraction comprising isobutene and 1-butene and a second fraction comprising 2-butene; and
contacting at least a portion of the first fraction with a first metathesis catalyst in a first metathesis reaction zone;
recovering an effluent from the first metathesis reaction zone comprising at least one of ethylene, propylene, unreacted isobutene, C5 olefins, and C6 olefins;
contacting at least a portion of the second fraction and at least a portion of the ethylene in the effluent with a second metathesis catalyst in a second metathesis reaction zone;
recovering an effluent from the second reaction zone comprising at least one of unreacted ethylene, propylene, unreacted 2-butene,
fractionating the effluent from the first metathesis reaction zone and the effluent from the second metathesis reaction zone to recover an ethylene fraction, a propylene fraction, one or more C4 fractions, and a fraction comprising at least one of C5 and C6 olefins.

8. The process of claim 7, wherein the first fraction further comprises isobutane, the process further comprising:
fractionating the first fraction to recover an isobutane fraction and a fraction comprising isobutene and 1-butene; and
feeding the fraction comprising isobutene and 1-butene to the first metathesis reaction zone as the at least a portion of the first fraction.

9. A process for the production of propylene, comprising:
fractionating a mixed C4 hydrocarbon stream to recover a first fraction comprising isobutene and a second fraction comprising 2-butene;
feeding a portion of the second fraction to an isomerization reaction zone to convert 2-butene to 1-butene, recovering an effluent from the isomerization reaction zone, and feeding the effluent from the isomerization reaction zone to the fractionating a mixed C4 stream;
contacting at least a portion of the first fraction with a first metathesis catalyst in a first metathesis reaction zone;
recovering an effluent from the first metathesis reaction zone comprising at least one of ethylene, propylene, unreacted isobutene, C5 olefins, and C6 olefins;
contacting at least a portion of the second fraction and at least a portion of the ethylene in the effluent with a second metathesis catalyst in a second metathesis reaction zone;
recovering an effluent from the second reaction zone comprising at least one of unreacted ethylene, propylene, unreacted 2-butene,
fractionating the effluent from the first metathesis reaction zone and the effluent from the second metathesis reaction zone to recover an ethylene fraction, a propylene fraction, one or more C4 fractions, and a fraction comprising at least one of C5 and C6 olefins.

10. The process of claim 9, further comprising feeding the ethylene fraction to the second metathesis reaction zone as the at least a portion of the ethylene in the effluent from the first metathesis reaction zone.

11. The process of claim 9, further comprising recycling the one or more C4 fractions to at least one of the first metathesis reaction zone and the second metathesis reaction zone.

12. The process of claim 9 wherein the first fraction further comprises isobutane, the process further comprising:
fractionating the first fraction to recover an isobutane fraction and a fraction comprising isobutene and 1-butene; and
feeding the fraction comprising isobutene and 1-butene to the first metathesis reaction zone as the at least a portion of the first fraction.

* * * * *